(12) United States Patent
Neumann et al.

(10) Patent No.: US 8,697,871 B2
(45) Date of Patent: Apr. 15, 2014

(54) INTEGRATED PHOTOACTIVE AGENTS AND USES THEREOF

(71) Applicant: MediBeacon Development, LLC, St. Louis, MO (US)

(72) Inventors: William L. Neumann, St. Louis, MO (US); Richard B. Dorshow, St. Louis, MO (US)

(73) Assignee: Medibeacon, LLC, St. Louis, MO (US)

( * ) Notice: Subject to any disclaimer, the term of this patent is extended or adjusted under 35 U.S.C. 154(b) by 0 days.

(21) Appl. No.: 13/675,534

(22) Filed: Nov. 13, 2012

(65) Prior Publication Data

US 2013/0136698 A1 May 30, 2013

Related U.S. Application Data

(62) Division of application No. 12/669,497, filed as application No. PCT/US2008/071700 on Jul. 31, 2008, now Pat. No. 8,350,032.

(60) Provisional application No. 60/952,915, filed on Jul. 31, 2007.

(51) Int. Cl.
*C07D 241/28* (2006.01)

(52) U.S. Cl.
USPC .......................................................... 544/407

(58) Field of Classification Search
USPC .......................................................... 544/407
See application file for complete search history.

*Primary Examiner* — Brian McDowell
(74) *Attorney, Agent, or Firm* — Dennis A. Bennett; Gale W. Starkey

(57) ABSTRACT

The present invention discloses a number of photoactive compounds designed to bind and inhibit serine proteases. Compounds disclosed herein may be utilized in a number of appropriate medical diagnostic and/or therapeutic procedures such as the monitoring of hemostasis, imaging and/or treatment of vulnerable plaques, and/or tumor imaging and/or treatment.

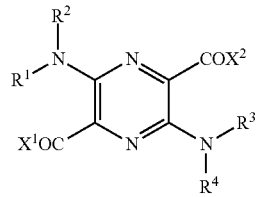

4 Claims, 4 Drawing Sheets

INTEGRATED PHOTOACTIVE AGENTS AND USES THEREOF

CROSS-REFERENCES TO RELATED APPLICATIONS

This application is a divisional of U.S. patent application Ser. No. 12/669,497, filed Jul. 31, 2008, which application claims priority to U.S. provisional patent application Ser. No. 60/952,915, filed Jul. 31, 2007, each of which is incorporated herein in its entirety by this reference thereto.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

This invention relates photoactive compounds for use in medical diagnostic and/or therapeutic procedures.

2. Description of Related Art

Publications are referenced throughout the specification in parenthesis. Full citations corresponding to the cited references are listed following the detailed description.

Patients at risk for clotting- and/or bleeding-related adverse events tend to be monitored using aPTT (activated partial thromboplastin time) and PT (prothrombin time) blood tests (Bajaj et al and Kher et al). Generally, patients on heparin are closely monitored by frequent measurement of aPTT to indicate the degree to which the extrinsic coagulation cascade is activated. Patients on Coumadin® are monitored by frequent measurement of PT (Riley et al) to evaluate the contributions of the extrinsic pathways. Both tests require blood samples that are sent to the hospital laboratory for analysis. Turnaround times are generally lengthy enough that a patient's hemostasis can change significantly during the analysis period. As such, it would be beneficial to develop compounds for use in monitoring hemostasis that would shorten the turn-around time between testing and results.

BRIEF SUMMARY OF THE INVENTION

A first aspect of the invention is directed to a compound that includes a pyrazine ring. A carbon of this pyrazine ring has a substituent bonded thereto that includes a group that binds to and inhibits a serine protease.

With regard to this first aspect of the invention, the serine protease may be Tissue Factor/Factor VIIa in some embodiments. In some embodiments, the serine protease may be Factor Xa.

The group that binds to and inhibits a serine protease may be any appropriate group that provides the required binding and inhibitory functions when the substituent is bound to the ring. Tests to determine these binding and inhibitory functions are known in the art. In some embodiments, the group may be an amidine. For instance, in some embodiments, the group may be a mono-benzamidine. In some embodiments, the group may be a guanidine.

Still referring to the first aspect of the invention, the pyrazine ring may have a number of substituents bonded thereto that each include at least one group that binds to and inhibits one or more serine proteases. For instance, in some embodiments, the pyrazine ring may have a first substituent bonded to a first carbon of the ring and a second substituent bonded to a second carbon of the pyrazine ring. These first and second substituents may be in any appropriate orientation relative to one another (e.g., ortho, meta, or para). Further, each of the first and second substituents includes at least one (e.g., one, two, three, four, five, etc.) group that binds to and inhibits serine protease(s). In the case that a given substituent includes multiple groups, each of the groups may be identical or different from one another. Further, the group(s) associated with the first substituent may be the same as or different from the group(s) associated with the second substituent.

In some embodiments, the pyrazine ring may have a first substituent bonded to a first carbon of the ring, a second substituent bonded to a second carbon of the pyrazine ring, a third substituent bonded to a third carbon of the pyrazine ring, and a fourth substituent bonded to a fourth carbon of the pyrazine ring. In some embodiments, three of the first, second, third, and fourth substituents includes at least one (e.g., one, two, three, four, five, etc.) group that binds to and inhibits serine protease(s). In some embodiments, all four of the first, second, third, and fourth substituents includes at least one (e.g., one, two, three, four, five, etc.) group that binds to and inhibits serine protease(s). In the case that a given substituent includes multiple groups, each of the groups may be identical or different from one another. Further, the group(s) associated with a particular substituent may be the same as or different from the group(s) associated with any other substituent(s).

In some embodiments of the first aspect, the compound may include or exhibit a fully symmetric di-basic structure. In other embodiments, the compound may include or exhibit a reverse-turn mimetic structure.

A second aspect of the invention is directed to compounds of Formula 1 below.

Formula 1

Each of $R^1$, $R^2$, $R^3$, $R^4$, $X^1$, and $X^2$ is independently hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, C1-C6 aminoalkyl, C5-C10 aryl, $-(CH_2)_m-Y-C(=NH)NH_2$, $-(CH_2)_m(CHR^5)_n-Y-C(=NH)NH_2$, $-(CH_2)_m(CHR^5)_n-Y-NHC(=NH)NH_2$, $-(CH_2)_m-Y-NHC(=NH)NH_2$, $-O-Y-C(=NH)NH_2$, $-O-Y-NHC(=NH)NH_2$, $-N(R^6)-Y-C(=NH)NH_2$, or $-N(R^7)-Y-NHC(=NH)NH_2$. However, at least one of $R^1$, $R^2$, $R^3$, $R^4$, $X^1$, or $X^2$ must be $-(CH_2)_m-Y-C(=NH)NH_2$, $-(CH_2)_m(CHR^5)_n-Y-C(=NH)NH_2$, $-(CH_2)_m(CHR^5)_n-Y-NHC(=NH)NH_2$, $-(CH_2)_m-Y-NHC$ (=NH)NH$_2$, —O—Y—C(=NH)NH$_2$, —O—Y—NHC(=NH)NH$_2$, —N(R$^6$)—Y—C(=NH)NH$_2$, or —N(R$^7$)—Y—NHC(=NH)NH$_2$.

Y is any of the substituents listed below:

For instance, Y may be an alkyl substituent in some embodiments and a benzene (or other homocyclic or heterocyclic) substituent in other embodiments.

Each of 'm,' 'n,' and 'p' is independently 0, 1, 2, 3, 4, 5, or 6.

R$^5$ is hydroxyl, C1-C6 hydroxyalkyl, carboxyl, C1-C6 carboxyalkyl, amino, or C1-C6 aminoalkyl. For instance, in some embodiments, R$^5$ is carboxyl.

Each of R$^6$ and R$^7$ is independently hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, C1-C6 aminoalkyl, or C5-C10 aryl.

In some embodiments of the second aspect, each of R$^1$, R$^2$, R$^3$, R$^4$, and X$^1$ may be hydrogen, while X$^2$ is —(CH$_2$)$_m$—Y—C(=NH)NH$_2$, —(CH$_2$)$_m$—Y—NHC(=NH)NH$_2$, —(CH$_2$)m(CHR$^5$)n-Y—C(=NH)NH$_2$, —(CH$_2$)$_m$(CHR$^5$)$_n$—Y—NHC(=NH)NH$_2$, —N(R$^6$)—Y—C(=NH)NH$_2$, or —N(R$^7$)—Y—NHC(=NH)NH$_2$. For example, each of R$^1$, R$^2$, R$^3$, R$^4$, and X$^1$ may be hydrogen, while X$^2$ may simply be —(CH$_2$)$_m$—Y—C(=NH)NH$_2$, —(CH$_2$)$_m$(CHR$^5$)$_n$—Y—NHC(=NH)NH$_2$, or —N(R$^6$)—Y—C(=NH)NH$_2$.

In some embodiments, each of R$^1$, R$^2$, R$^3$, and R$^4$ may be hydrogen, while each of X$^1$ and X$^2$ may independently be —(CH$_2$)$_m$—Y—C(=NH)NH$_2$, —(CH$_2$)$_m$—Y—NHC(=NH)NH$_2$, —(CH$_2$)$_m$(CHR$^5$)$_n$—Y—C(=NH)NH$_2$, —(CH$_2$)$_m$(CHR$^5$)$_n$—Y—NHC(=NH)NH$_2$, —N(R$^6$)—Y—C(=NH)NH$_2$, or —N(R$^7$)—Y—NHC(=NH)NH$_2$. For example, each of R$^1$, R$^2$, R$^3$, and R$^4$ may be hydrogen, while each of X$^1$ and X$^2$ may independently be —(CH$_2$)$_m$—Y—C(=NH)NH$_2$, —(CH$_2$)$_m$(CHR$^5$)$_n$—Y—NHC(=NH)NH$_2$, or —N(R$^6$)—Y—C(=NH)NH$_2$.

In any of the embodiments of the second aspect mentioned above, R$^6$ may be any appropriate substituent (e.g., hydrogen).

Still referring to the various possible refinements of the compounds of Formula 1, in some embodiments, each of R$^2$, R$^3$, R$^4$, X$^1$, and X$^2$ may be hydrogen, while R$^1$ may be —(CH$_2$)$_m$—Y—C(=NH)NH$_2$, —(CH$_2$)$_m$—Y—NHC(=NH)NH$_2$, —(CH$_2$)$_m$(CHR$^5$)$_n$—Y—C(=NH)NH$_2$, or —(CH$_2$)$_m$(CHR$^5$)$_n$—Y—NHC(=NH)NH$_2$. For example, each of R$^2$, R$^3$, R$^4$, X$^1$, and X$^2$ may be hydrogen, while R$^1$ may be —(CH$_2$)$_m$—Y—C(=NH)NH$_2$ or —(CH$_2$)$_m$(CHR$^5$)$_n$—Y—NHC(=NH)NH$_2$.

In some embodiments, each of R$^2$, R$^4$, X$^1$, and X$^2$ may be hydrogen, while each of R$^1$ and R$^3$ may independently be —(CH$_2$)$_m$—Y—C(=NH)NH$_2$, —(CH$_2$)$_m$—Y—NHC(=NH)NH$_2$, —(CH$_2$)$_m$(CHR$^5$)$_n$—Y—C(=NH)NH$_2$, or —(CH$_2$)$_m$(CHR$^5$)$_n$—Y—NHC(=NH)NH$_2$. For instance, each of R$^2$, R$^4$, X$^1$, and X$^2$ may be hydrogen, while each of R$^1$ and R$^3$ may independently be —(CH$_2$)$_m$—Y—C(=NH)NH$_2$ or —(CH$_2$)$_m$(CHR$^5$)$_n$—Y—NHC(=NH)NH$_2$.

'm' may be any appropriate integer. For instance, in various embodiments, 'm' may be of any of the following inclusive ranges: 0-5, 0-4, 0-3, 0-2, 0-1, 1-6, 1-5, 1-4, 1-3, 1-2, 2-6, 2-5, 2-4, 2-3, 3-6, 3-5, 3-4. In one particular exemplary embodiment, 'm' may be 0, 1, 2, or 3.

Likewise, 'n' may be any appropriate integer. For instance, in various embodiments, 'n' may be of any of the following inclusive ranges: 0-5, 0-4, 0-3, 0-2, 0-1, 1-6, 1-5, 1-4, 1-3, 1-2, 2-6, 2-5, 2-4, 2-3, 3-6, 3-5, 3-4. In one particular exemplary embodiment, 'n' may be 0, 1, 2, or 3.

Further, 'p' may be any appropriate integer. For instance, in various embodiments, 'p' may be of any of the following inclusive ranges: 0-5, 0-4, 0-3, 0-2, 0-1, 1-6, 1-5, 1-4, 1-3, 1-2, 2-6, 2-5, 2-4, 2-3, 3-6, 3-5, 3-4. In one particular exemplary embodiment, 'p' may simply be 1.

In some embodiments, the utility of compounds of Formula 1 in medical procedures is due to their ability to bind to and inhibit serine proteases (e.g., Tissue Factor/Factor VIIa and/or Factor Xa). Since such compounds inhibit serine proteases, these compounds may also be utilized to provide therapeutic affect (i.e., may be utilized in medical drug therapy).

Compounds of the first and second aspects of the invention may be used in any of a number of appropriate medical procedures. For instance, in some embodiments, such compounds may be utilized in a medical diagnostic procedure such as monitoring hemostasis in a patient, imaging vulnerable (e.g., unstable) plaques, and/or tumor imaging. In some embodiments, such compounds may be utilized in a dual-role in medical diagnostic procedure as well as in medical drug therapy (e.g., monitoring and prevention of clotting, imaging vulnerable (e.g., unstable) plaques while reducing likelihood of undesired clots/vascular occlusions, and/or tumor imaging and therapy.

In some embodiments, the compound of the first and/or second aspects may be encapsulated into a micelle, a liposome, a nanoparticle (e.g., a shell cross-linked nanoparticle), a dendrimer, a dendron, a microcapsule, or other organized microparticle. In some embodiments, a compound of the first and/or second aspect may be chemically conjugated to a nanoparticle (e.g., a shell cross-linked nanoparticle), a dendrimer, or a dendron.

A third aspect of the invention is directed to a medical formulation that includes: 1) any compound of the first and/or second aspect; and 2) a pharmaceutically acceptable buffer, surfactant, excipient, thixotropic agent, flavoring agent, stabilizing agent, skin penetration enhancing agent, or any combination thereof.

DETAILED DESCRIPTION OF THE INVENTION

The invention includes integrated photoactive agents (herein also referred to as "photoactive agents") that bind to and inhibit serine proteases, as well as the manufacture and use of such agents. Some of these integrated photoactive agents may be characterized as small molecules having a molecular weight of less than about 1000 Daltons. Photoactive agents of the invention may be manufactured by rendering a photoactive scaffold able to bind a serine protease. Once synthesized, the integrated photoactive agent can be administered to a patient and utilized as an optical diagnostic agent and/or a therapeutic drug. For instance, in one embodiment, integrated photoactive agents of the present invention may be utilized to monitor hemostasis. In another embodiment, integrated photoactive agents of the present invention may be used in the imaging of vulnerable plaques. In yet another embodiment, integrated photoactive agents of the present invention may be utilized in tumor imaging.

Serine proteases (referred to by some as "serine endopeptidases") are a class of enzymes that play a significant role, inter alia, in the clotting process. In particular, some serine proteases play a significant role in the extrinsic coagulation cascade. Examples of serine proteases include thrombin (activated Factor II [IIa]), and thrombokinase (activated Factor X [Xa]), Factor VII (activated Tissue Factor/Factor VIIa). In many serine proteases, aspartate-189 is the primary recognition site residue for binding to the S1 pocket of the enzyme but there are a number of other important interactions within the S1', S2, and S3 sites of the enzyme that are desirable for high potency binding (nanomolar affinity Neumann et al *J. Med. Chem.* 2003, 46, 4050). Many compounds of the present invention include a design in which the scaffold is both photoactive and displays the P1 substituent appropriately to bind to the aspartate-189 residue of serine proteases. In addition, the photoactive scaffold may have functionality that can provide additional interactions with other residues surrounding the catalytic apparatus. In this regard, it may be said that the photoactive scaffold is integrated with ligand binding properties. In one mechanistic characterization, it may be said that compounds of the invention bind to and inhibit Tissue Factor/Factor VIIa and/or Factor Xa, and thus, inhibit production of Thrombin (e.g., via the extrinsic cascade).

Integrated photoactive agents of the present invention tend to have absorption, excitation, and emission wavelengths that are all within the near-infrared (NIR) or visible spectrum of about 350 nm or greater. This is beneficial for diagnostic procedures since visible and NIR light is not likely to damage tissue. In contrast, ultraviolet (UV) light that has a wavelength of less than about 350 nm can cause tissue damage. Light having a wavelength of about 350 nm or greater tends to penetrate into tissues thereby permitting diagnostic procedures to be conducted in tissues of interest that may not be reachable using UV wavelengths that are less than about 350 nm. In one embodiment, compounds of the invention have absorption, excitation, and emission wavelengths that are all between about 350 nm and about 1200 nm. In another embodiment, compounds of the invention may have absorption, excitation, and emission wavelengths that are all between about 400 nm and about 900 nm.

Synthesis and use of compounds disclosed herein may be performed in a variety of ways. In one embodiment, known serine protease binding moieties (fragment based lead design) are attached to a photoactive group or molecule (e.g., a pyrazine group). It is presently believed that pyrazines are particularly suited for this purpose due to their desirable photophysical properties as well as the ability of some to serve as isosteric replacements for aromatic motifs. In many cases, this would allow the substitution of a photoactive pyrazine core for a non-photoactive aryl or heteroaryl core in known drugs or drug lead candidates. The resulting compound would then possess the biological activity of the drug and the photoactivity of the pyrazine. Hence, the photonic nature of the pyrazine system is integrated within the drug itself.

Figure 1:
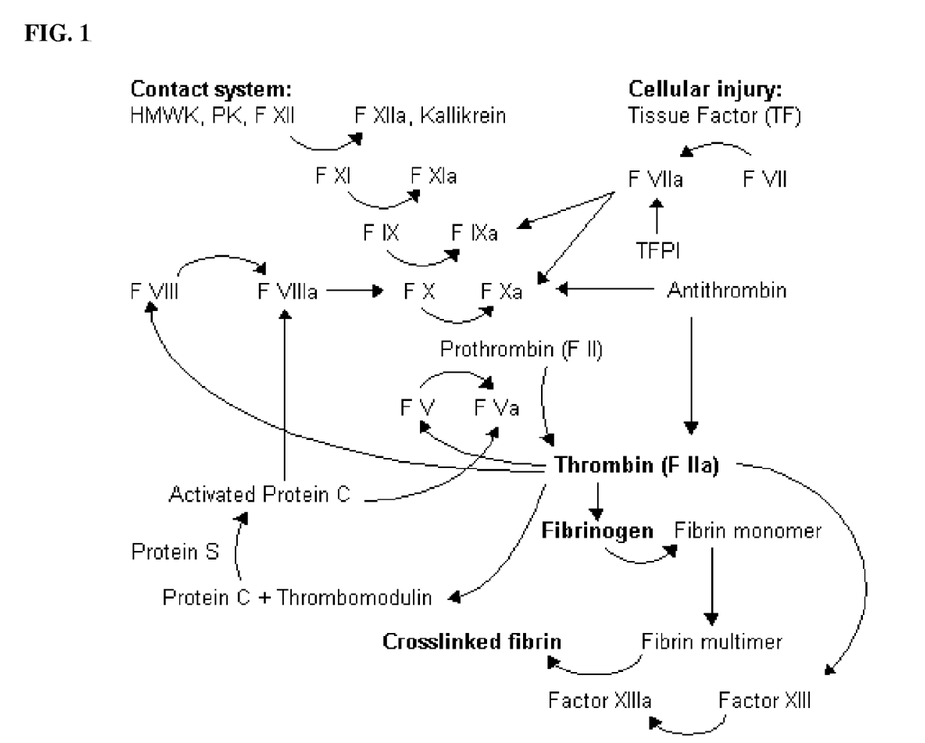
FIG. 1 is an illustration of the coagulation cascade.

For compounds of the present invention, the target tends to be serine proteases involved in the coagulation cascade, illustrated in FIG. 1. Examples of pharmacophores that bind to serine proteases include, but are not limited to, amidines and guanidine. One or more pharmacophore(s) are attached to the photoactive molecule in appropriate places such that both photoactivity and bioactivity will not be disrupted to the extent that the resulting agent completely loses its photoactivity or binding properties. The resulting integrated photoactive agent may be administered to a patent in a diagnostically effective amount such as to enable detection of the photoactive agent within the patient. After a period of time has lapsed for the agent to bind to serine protease, the whole body or a target tissue of a patient may be exposed to light of between about 350 nm and about 1200 nm wavelength. In one example, the whole body or a target tissue of a patient may be exposed a light of between about 400 nm and about 900 nm wavelength. Light emanates from the compound within the patient as a result of absorption and excitation properties of the compound. This emanating light may be detected by utilizing an appropriate detector that may be designed and/or chosen based on its ability to detect the specific wavelength(s) of the light emanating from the compound within the patient. By determining the location and strength (e.g., intensity) of light emanating from the compound within the patient, a diagnosis may be made.

Figure 2:
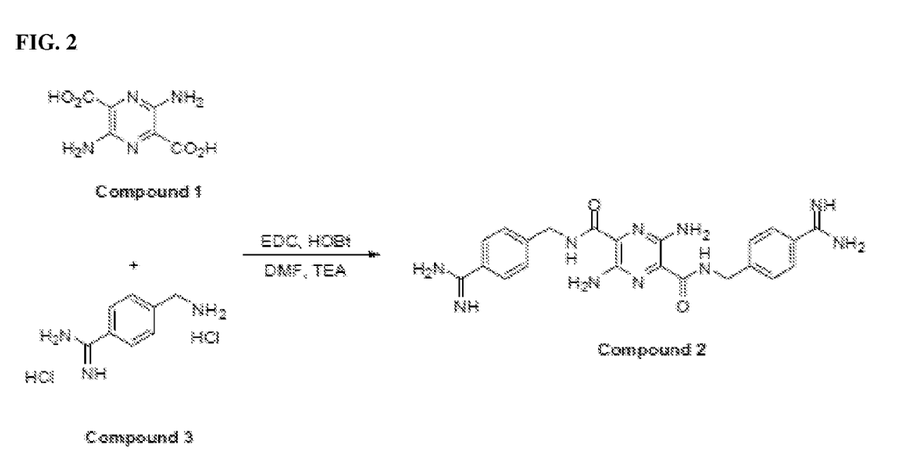
FIG. 2 is an example of the general synthesis of integrated photoactive serine protease inhibitors of the present invention.

The synthesis of an integrated photoactive agent of the present invention may be accomplished using this disclosure in combination with known scientific principles. One exemplary method of manufacturing a compound of the invention is outlined in FIG. 2.

In one embodiment, an integrated photoactive agent of the invention comprises a photoactive group of Formula 1, Formula 1 which serves as a molecular scaffold upon which at least one pharmacophore that binds to serine proteases is attached at the $R^1$, $R^2$, $R^3$, $R^4$, $X^1$, and/or $X^2$ position(s) to create an integrated photoactive serine protease binding agent (which is also a serine protease inhibitor). In one example, the molecular scaffold of Formula 1 is 2,5-diamino-3,6-pyrazinedicarboxylic acid. In another example, the pharmacophores(s) is(are) an amidine and/or a guanidine moiety, each of which may be attached to the pyrazine structure of Formula 1 at any one or more of the positions designated by $R^1$, $R^2$, $R^3$, $R^4$, $X^1$, or $X^2$.

Figure 3:
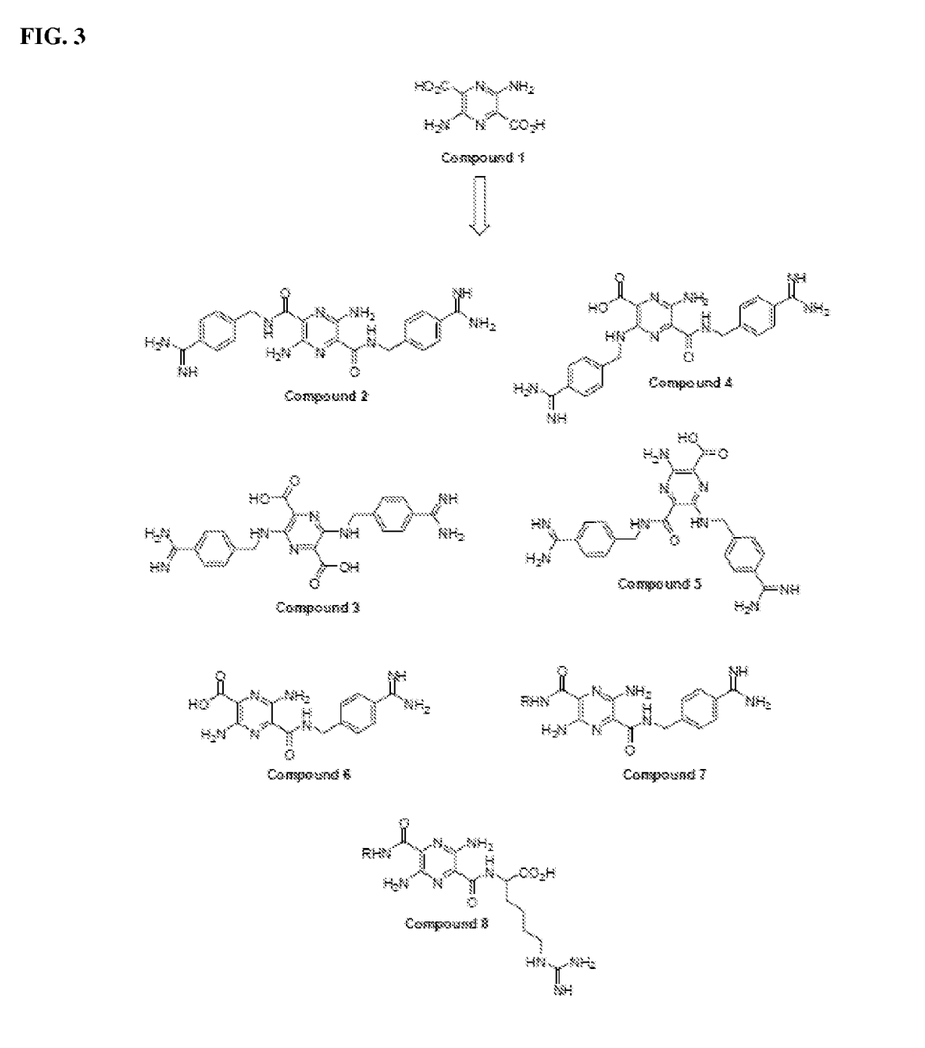
FIG. 3 provides structural examples of integrated photoactive serine protease inhibitors.

FIG. 3 provides non-limiting examples of integrated photoactive agents of the present invention that are represented by Compounds 2-8. Compounds 2 and 3 are examples of fully symmetric di-basic structures, Compounds 4 and 5 are examples of reverse-turn mimetic structures, Compounds 6 and 7 are examples of mono-benzamidine-containing compounds, and Compound 8 is an example of an integrated photoactive agent that comprises a guanidine moiety as its binding moiety.

The benzamidine moiety serves as an arginine mimetic, as these hydrolytic enzymes recognize a particular arginine residue to effect cleavage and activation of the corresponding proenzyme in the coagulation cascade. Thus, molecules built around the benzamidine are desirable binding moieties for serine protease inhibitors.

In one embodiment, the photoactive compound is represented by Formula 1, wherein $R^1$, $R^2$, $R^3$, $R^4$, $X^1$, and $X^2$ are independently hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, C1-C6 aminoalkyl, C5-C10 aryl, —(CH$_2$)$_m$—Y—C(=NH)NH$_2$, —(CH$_2$)$_m$(CHR$^5$)$_n$—Y—C(=NH)NH$_2$, —(CH$_2$)$_m$(CHR$^5$)$_n$—Y—NHC(=NH)NH$_2$, —(CH$_2$)$_m$—Y—NHC(=NH)NH$_2$, —O—Y—C(=NH)NH$_2$, —O—Y—NHC(=NH)NH$_2$, —N(R$^6$)—Y—C(=NH)NH$_2$, or —N(R$^7$)—Y—NHC(=NH)NH$_2$. In some embodiments, at least one of $R^1$, $R^2$, $R^3$, $R^4$, $X^1$, or $X^2$ must be —(CH$_2$)$_m$—Y—C(=NH)NH$_2$, —(CH$_2$)m(CHR$^5$)$_n$—Y—C(=NH)NH$_2$, —(CH$_2$)m(CHR$^5$)$_n$—Y—NHC(=NH)NH$_2$, —(CH$_2$)$_m$Y—NHC(=NH)NH$_2$, —O—Y—C(=NH)NH$_2$, —O—Y—NHC(=NH)NH$_2$, —N(R$^6$)—Y—C(=NH)NH$_2$, or —N(R$^7$)—Y—NHC(=NH)NH$_2$. Y is any of the substituents listed below:

The subscripts 'm,' 'n,' and 'p' independently range from 0 to 6, inclusive. $R^5$ is hydroxyl, C1-C6 hydroxyalkyl, carboxyl, C1-C6 carboxyalkyl, amino, or C1-C6 aminoalkyl. $R^6$ and $R^7$ are independently hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, C1-C6 aminoalkyl, or C5-C10 aryl.

In another embodiment, the photoactive compound is represented by Formula 1, wherein: $R^1$ to $R^4$, $R^6$, and $X^1$ are hydrogens; $R^5$ is carboxyl; $X^2$ is —(CH$_2$)$_m$—Y—C(=NH)NH$_2$, —(CH$_2$)$_m$—Y—NHC(=NH)NH$_2$, (CH$_2$)$_m$(CHR$^5$)$_n$—Y—C(=NH)NH$_2$, —(CH$_2$)$_m$(CHR$^5$)$_n$—Y—NHC(=NH)NH$_2$, —N(R$^6$)—Y—C(=NH)NH$_2$, or —N(R$^7$)—Y—NHC(=NH)NH$_2$; 'm' and 'n' independently range from 0 to 3; 'p' is 1; and Y is

In another embodiment, the photoactive compound is represented by Formula 1, wherein: $R^1$ to $R^4$ and $R^6$ are hydrogens; $R^5$ is carboxyl; $X^1$ and $X^2$ are independently —(CH$_2$)$_m$—Y—C(=NH)NH$_2$, —(CH$_2$)$_m$—Y—NHC(=NH)NH2, —(CH$_2$)$_m$(CHR$^5$)$_n$—Y—C(=NH)NH$_2$, —(CH$_2$)$_m$(CHR$^5$)$_n$—Y—NHC(=NH)NH$_2$, —N(R$^6$)—Y—C(=NH)NH$_2$, or —N(R$^7$)—Y—NHC(=NH)NH$_2$; 'm' and 'n' independently range from 0 to 3; 'p' is 1; and Y is

In another embodiment, the photoactive compound is represented by Formula 1, wherein: $R^2$ to $R^4$, $X^1$, and $X^2$ are hydrogens; $R^1$ is —(CH$_2$)$_m$—Y—C(=NH)NH$_2$, —(CH$_2$)$_m$—Y—NHC(=NH)NH$_2$, —(CH$_2$)$_m$(CHR$^5$)$_n$—Y—C(=NH)NH$_2$, or —(CH$_2$)$_m$(CHR$^5$)$_n$—Y—NHC(=NH)NH$_2$; 'm' and 'n' independently range from 0 to 3; 'p' is 1; and Y is

In another embodiment, the photoactive compound is represented by Formula 1, wherein: $R^2$, $R^4$ to $R^6$, $X^1$, and $X^2$ are hydrogens; $R^1$ and $R^3$ are independently —(CH$_2$)$_m$—Y—C(=NH)NH$_2$, —(CH$_2$)$_m$—Y—NHC(=NH)NH$_2$, —(CH$_2$)$_m$(CHR$^5$)$_n$—Y—C(=NH)NH$_2$, or —(CH$_2$)$_m$(CHR$^5$)$_n$—Y—NHC(=NH)NH$_2$; 'm' and 'n' independently range from 0 to 3; 'p' is 1; and Y is In another embodiment, the photoactive compound is represented by Formula 1, wherein: $R^1$ to $R^4$, $R^6$, and $X^1$ are hydrogens; $R^5$ is carboxyl; $X^2$ is —(CH$_2$)$_m$—Y—C(=NH)NH$_2$, —(CH$_2$)$_m$(CHR$^5$)$_n$—Y—NHC(=NH)NH$_2$, or —N(R$^6$)—Y—C(=NH)NH$_2$; 'm' and 'n' independently range from 0 to 3; 'p' is 1; and Y is In another embodiment, the photoactive compound is represented by Formula 1, wherein: $R^1$ to $R^4$ and $R^6$ are hydrogens; $R^5$ is carboxyl; $X^1$ and $X^2$ are independently —(CH$_2$)$_m$—Y—C(=NH)NH$_2$, —(CH$_2$)$_m$(CHR$^5$)$_n$—Y—NHC(=NH)NH$_2$, or —N(R$^6$)—Y—C(=NH)NH$_2$; 'm' and 'n' independently range from 0 to 3; 'p' is 1; and Y is In another embodiment, the photoactive compound is represented by Formula 1, wherein: $R^2$ to $R^4$, $X^1$, and $X^2$ are hydrogens; $R^1$ is —(CH$_2$)$_m$—Y—C(=NH)NH$_2$, or —$(CH_2)_m$ $(CHR^5)_n$—Y—NHC(=NH)$NH_2$; 'm' and 'n' independently range from 0 to 3; 'p' is 1; and Y is In another embodiment, the photoactive compound is represented by Formula 1, wherein: $R^2$, $R^4$ to $R^6$, $X^1$, and $X^2$ are hydrogens; $R^1$ and $R^3$ are independently —$(CH_2)_m$—Y—C(=NH)$NH_2$ or —$(CH_2)_m$$(CHR^5)_n$—Y—NHC(=NH)$NH_2$; 'm' ranges from 0 to 3; 'p' is 1; and Y is In another embodiment, the photoactive compound is a fully symmetric di-basic serine protease inhibitor, such as Compound 2 or Compound 3 below.

Compound 2

Compound 3

In another embodiment, the photoactive compound is a reverse-turn mimetic structure such as Compound 4 or Compound 5 below.

Compound 4

Compound 5

In another embodiment, the photoactive compound is a mono-benzamidine-containing compound such as Compound 6 or Compound 7 below.

Compound 6

Compound 7

In another embodiment, the photoactive compound is a guanidine derivative such as Compound 8 below.

Compound 8

Compounds of the present invention possess both thrombin inhibitory activity (e.g., through inhibition of Tissue Factor/Factor VIIa and/or Factor Xa) and a fluorescent scaffold. If the clotting cascades of FIG. 1 have been activated (e.g., due to pathogenic events such as trauma, deep vein thrombosis, plaque rupture, cardiac arrhythmias etc.), thrombin concentrations in the blood will be increased. After being administered to a patient (e.g., intravenously and/or intraarterially injected into a patient's blood stream), a compound of the present invention binds to Factor Xa and/or Tissue Factor/Factor VIIa and is detectable via a shift in fluorescence emission versus that of the unbound fraction of the compound.

In this regard, it is known from fluorescence and Raman spectroscopic studies of green fluorescent and red fluorescent proteins as well as model compounds, that the chromophore triad displays remarkably different photophysical properties when buried inside the protein versus diffusing freely in solvent. The energy of reorganizing the environment to accommodate the excited state of the photoactive serine protease inhibitor is quite different when the molecule is bound in the active site of the enzyme versus circulating freely in the blood. Thus, free versus bound inhibitors display different absorption and emission wavelengths. This phenomenon allows for the possibility of accurate real-time measurement of Tissue Factor/Factor VIIa inhibition and/or Factor Xa inhibition and, therefore, ultimately, thrombin production (e.g., concentration) in blood by a ratiometric paradigm. The concentrations and/or fluorescence measurement ratios for Tissue Factor/Factor VIIa or Factor Xa inhibition can (if desired) be cross-correlated with actual PT (prothrombin time) measurements in animals or patients to develop a mathematical model for accuracy. The concentrations and/or fluorescence measurement ratios can thus be used to determine whether or not a patient is experiencing an enhanced propensity for a thrombotic event and enable healthcare personnel to take corrective action.

A fiber optic laser apparatus can be used at the bed-side, in the surgical suite, or on board emergency transport vehicles to monitor patient coagulation hemostasis in real time. This methodology potentially allows for precise monitoring of patients at risk for clotting related events. Typically, such patients are maintained on powerful anticoagulants (e.g., warfarin or heparin) and are therefore at risk of potentially catastrophic bleeding events.

It is well established that vulnerable plaque rupture is the main cause of acute coronary syndromes. The thrombogenicity of these plaques tends to correlate directly with the Tissue Factor level within them. Arterial thrombosis therefore frequently tends to be a consequence of plaque rupture, which exposes that Tissue Factor to circulating blood resulting in the Tissue Factor combining with Factor VII to trigger coagulation (Moreno, P. R. et al *Circulation* 1996, 94. 3090 and Tanner, F. C. et al *Circulation* 2006, 113, 722). It is believed that micro-ruptures can expose Tissue Factor on the surfaces of vulnerable plaques triggering an unstable pre-thrombogenic situation. Administration of an integrated photonic Tissue Factor/Factor VIIa inhibitor such as those described herein would thus provide a way to monitor and image these unstable plaques prior to a catastrophic rupture event. The integrated photonic Tissue Factor/Factor VIIa inhibitor would accumulate at the micro-rupture sites by binding to surface adhered Tissue Factor/Factor VIIa and be visible by use of a catheter or other appropriate detection device (e.g., fiber optic laser apparatus). Since these photoactive agents are also pharmaceutically active, this methodology constitutes not only a diagnostic tool, but also a diagnostic-therapeutic pair.

With regard to tumor imaging, tumor metastases are typically dependent upon Tissue Factor over-expression. Indeed, metastatic cells may express up to 1000-fold more Tissue Factor than non-malignant counterparts (e.g., in colorectal and pulmonary cancers). In addition, tumor tissue is associated with the over-expression of vascular endothelial growth factor (VEGF), which is a factor important in the process of angiogenesis supporting tumor growth and metastasis. The expression of VEGF is therefore associated with endothelial permeability potentially enabling Tissue Factor exposure to circulating Factor VII. Thus, the administration of an integrated photonic Tissue Factor/Factor VIIa inhibitor would provide a way to monitor and image tumor boundaries on surfaces and sub-surfaces of tumor tissue exposed to blood. The integrated photonic Tissue Factor/Factor VIIa inhibitor would accumulate in the tumor via enhanced endothelial permeability induced by VEGF by binding to the exposed Tissue Factor/Factor VIIa and be visible by use of a catheter or other appropriate detection device (e.g., fiber optic laser apparatus). Since these photoactive agents are also pharmaceutically active, this methodology constitutes not only a diagnostic tool, but also a diagnostic-therapeutic pair.

Formulation

Integrated photoactive agents of the present invention can be formulated for enteral (oral or rectal), parenteral (e.g., intramuscular injection, intravenous injection, intraarterial injection), topical, transdermal, or subcutaneous administration. Topical, transdermal, and cutaneous delivery can include aerosols, creams, gels, emulsions, solutions, or suspensions. Delivery into and through the skin can be enhanced in accordance with known methods and agents such as transdermal permeation enhancers, for example, "azone", N-alkylcyclic amides, dimethylsulfoxide, long-chained aliphatic acids (C10), etc. (Gennaro). Currently, preferred formulations for photoactive agents of the inventions are those that may be administered via injection (e.g., intramuscular injection, intravenous injection, intraarterial injection).

Preparation of pharmaceutically acceptable formulations can be accomplished according to methods known in the art (Gennaro). For instance, a formulation may be prepared using any of the integrated photoactive agents, along with pharmaceutically acceptable buffers, surfactants, excipients, thixotropic agents, flavoring agents, stabilizing agents, or skin penetration enhancing agents. If the inventive compound is water soluble, a solution in physiological saline may be administered. If the compound is not water soluble, the compound can be dissolved in a biocompatible oil (e.g., soybean oil, fish oil, vitamin E, linseed oil, vegetable oil, glyceride esters, long-chained fatty esters, etc.) and emulsified in water containing surface-active compounds (e.g., vegetable or animal phospholipids; lecithin; long-chained fatty salts and alcohols; polyethylene glycol esters and ethers; etc.), and administered as a topical cream, suspension, water/oil emulsion, or water/oil microemulsion.

The integrated photoactive agents of the invention may be encapsulated into micelles, liposomes, nanoparticles (e.g., shell cross-linked nanoparticles), dendrimers, dendrons, microcapsules, or other organized microparticles, and administered by any of the routes described previously. The integrated photoactive agents of the invention may be chemically conjugated to nanoparticles (e.g., shell cross-linked nanoparticles), dendrimers or dendrons for the purpose of simultaneously effecting an integrated photonic effect and a multivalent biological effect. These types of formulations may enhance stability of the agents in vivo. Exemplary encapsulation methods include, but are not limited, detergent dialysis, freeze drying, film forming, and injection (Janoff et al). Methods of making liposomes and encapsulating various molecules within them are well known in the art (Braun-Falco et al and Lasic et al).

Dosage

Integrated photoactive agents of the present invention may be administered in a single dose or in multiple doses to achieve the effective diagnostic and/or therapeutic objective. After administration, the integrated photoactive agent is allowed time to bind to serine proteases, and the selected target site is exposed to light with a sufficient power and intensity to detect light emanating from the compound within the patient's body to provide information that may be utilized by a healthcare provider (e.g., in making a diagnosis). Doses may vary widely depending upon, for example, the particular integrated photoactive agent employed, the areas (e.g., organs or tissues) to be examined, the equipment employed in the clinical procedure, the efficacy of the treatment achieved, and/or the like. For example, the dosage of the compound may vary from about 0.1 mg/kg body weight to about 500 mg/kg body weight in some embodiments. In other embodiments, the dosage of the compound may vary from about 0.5 to about 2 mg/kg body weight. In some embodiments for parenteral administration, a sterile solution or suspension comprises the integrated photoactive agent in a concentration range from about 1 nM to about 0.5 M. In some embodiments, a sterile solution or suspension comprises the integrated photoactive agent in a concentration range from about 1 µM to about 10 mM.

Administration

Once an integrated photoactive agent has been created, the agent is administered (e.g., via injection) to an individual. An appropriate amount of time may be given for the agent to bind to the desired serine protease(s) in the patient. It will be understood that administration of compounds and compositions of the present invention may be determined by an attending physician within the scope of sound medical judgment. The specific effective dose level for any particular patient may depend upon a variety of factors such as the disorder being treated/diagnosed, the severity of the disorder, activity of the specific compound employed, the specific composition employed, age, body weight, general health, sex, and/or diet of the patient. Detection of the integrated photoactive agent may be achieved by optical fluorescence, absorbance, and/or light scattering methods using invasive and/or non-invasive probes such as endoscopes, catheters, ear clips, hand bands, head bands, surface coils, finger probes, and/or the like (Muller et al). Imaging can be achieved using planar imaging, optical tomography, optical coherence tomography, endoscopy, photoacoustic technology, sonofluorescence technology, light scattering technology, laser assisted guided surgery (LAGS), confocal microscopy, dynamic organ function monitoring, and/or light scattering devices.

Abbreviations and Definitions

To facilitate understanding of the invention, a number of terms are defined below:

"Small molecule" refers to a molecule whose molecular weight is generally less than about 1000 Daltons.

"Diagnostically effective amount" is an amount of the substance in question which will, in a majority of patients, be an adequate quantity of substance to be able to detect the particular cells and/or enzymes, if present, in the patient to whom it is administered. The term "an effective amount" also implies that the substance is given in an amount which only causes mild or no adverse effects in the subject to whom it has been administered, or that the adverse effects may be tolerated from a medical and pharmaceutical point of view in the light of the severity of the disease for which the substance has been given.

"Photoactive group" or "photoactive moiety" refers to any functional group or moiety exhibiting an absorption, excitation, and emission maxima in the wavelength range of about 350-1200 nm. Such functional groups or moieties include, but are not limited to, fluorophores, chromophores, photosensitizers, and photoreactive moieties, wherein "fluorophores," "chromophores," "photosensitizers," and "photoreactive" moieties have meanings that are commonly understood in the art.

"Therapeutically-effective amount" refers to the amount of each agent that will achieve the goal of improvement in pathological condition severity and the frequency of incidence over treatment of each agent by itself, while avoiding adverse side effects typically associated with alternative therapies.

"Treatment" refers to any process, action, application, therapy, or the like, wherein a subject, including a human being, is provided medical aid with the object of improving the subject's condition, directly or indirectly, or slowing the progression of a pathological condition in the subject.

When introducing elements of the present invention or the embodiment(s) thereof, the articles "a", "an", and "the" are intended to mean that there are one or more of the elements. The terms "comprising", "including" and "having" are intended to be inclusive and mean that there may be additional elements other than the listed elements.

The following example illustrates specific embodiments of the invention. As would be apparent to skilled artisans, various changes and modifications are possible and are contemplated within the scope of the invention described.

EXAMPLES

Example 1

Preparation of 3,6-diamino-N2,N5-bis(4-carbamimidoylbenzyl)pyrazine-2,5-dicarboxamide (MP3117)

MP3117

A mixture of 3,6-diaminopyrazine-2,5-dicarboxylic acid (250 mg, 1.40 mmol), 4-(aminomethyl)-benzamidine dihydrochloride (619 mg, 2.80 mmol), HOBt-H$_2$O (628 mg, 4.10 mmol), EDC-HCl (790 mg, 4.10 mmol) and triethylamine (2 mL) was stirred together in DMF (20 mL) for 16 hours at room temperature. The mixture was concentrated to dryness and purified by medium pressure reversed phase chromagraphy (LiChroprep RP-18 Lobar (B) 25×310 mm—EMD chemicals 40-63 µm, ~70 g, 90/10 to 80/20 0.1% TFA-ACN) to afford 171 mg (27% yield) of example 1 as an orange foam: LCMS (5-95% gradient acetonitrile in 0.1% TFA over 10 min), single peak retention time=4.69 min on 250 C18 mm column, (M+H)$^+$=461.

Figure 4:
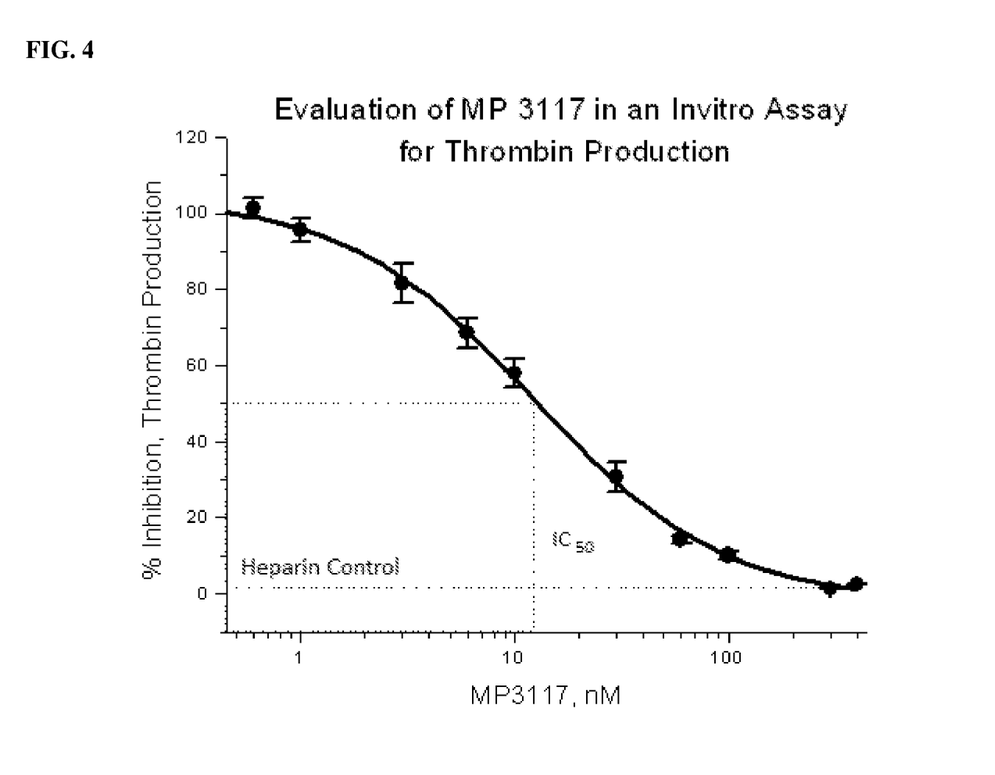
FIG. 4 is graph of results for an in vitro assay showing the effects of a compound of Formula I on thrombin production.

The compound (MP3117) of Example 1 was tested for its ability to inhibit the production of thrombin via activation of the extrinsic cascade. In particular, an assay that included a whole blood activity screen was performed. In this regard, nine aqueous solutions containing varying concentrations of the compound of Example 1 were tested for their ability to inhibit thrombin production when clotting was activated via the tissue factor pathway (in triplicate). The average of the data is shown in FIG. 4. The data from the assay was also utilized to extract the $IC_{50}$ for the compound. Incidentally, "$IC_{50}$" refers to the amount of a compound necessary to inhibit 50% of the active enzyme to which it binds. As shown in FIG. 4, the compound of Example 1 was shown to have an $IC_{50}=12.38\pm0.79$ nM.

What is claimed is:

1. A method of performing a diagnostic, imaging, or visualization procedure on a patient, comprising:

administering to a patient a diagnostically effective amount of a compound of Formula 1, Formula 1 wherein:

each of $R^1$, $R^2$, $R^3$, $R^4$, $X^1$, and $X^2$ is independently hydrogen, —OH, C1-C6 alkyl, C1-C6 acyl, C1-C6 alkoxycarbonyl, C1-C6 hydroxyalkyl, C1-C6 polyhydroxyalkyl, C1-C6 carboxyalkyl, C1-C6 aminoalkyl, C5-C10 aryl, —(CH$_2$)$_m$—Y—C(=NH)NH$_2$, —(CH$_2$)$_m$(CHR$^5$)$_n$—Y—C(=NH)NH$_2$, —(CH$_2$)$_m$(CHR$^5$)$_n$—Y—NHC(=NH)NH$_2$, —(CH$_2$)$_m$—Y—NHC(=NH)NH$_2$, —O—(CHR$^5$)$_n$—Y—C(=NH)NH$_2$, —O—(CHR$^5$)$_n$—Y—NHC(=NH)NH$_2$, —N(R$^6$)—(CH$_2$)$_m$(CHR$^5$)$_n$—Y—C(=NH)NH$_2$, or —N(R$^7$)—(CH$_2$)$_m$(CHR$^5$)$_n$—Y—NHC(=NH)NH$_2$;

Y is with the proviso that at least one of $R^1$, $R^2$, $R^3$, $R^4$, $X^1$, or $X^2$ is —(CH$_2$)$_m$—Y—C(=NH)NH$_2$, —(CH$_2$)$_m$(CHR$^5$)$_n$—Y—C(=NH)NH$_2$, —(CH$_2$)$_m$(CHR$^5$)$_n$—Y—NHC(=NH)NH$_2$, —(CH$_2$)$_m$—Y—NHC(=NH)NH$_2$, —O—(CHR$^5$)n—Y—C(=NH)NH$_2$, —O—(CHR$^5$)$_n$—Y—NHC(=NH)NH$_2$, —N(R$^6$)—(CH$_2$)$_m$(CHR$^5$)$_n$—Y—C(=NH)NH$_2$, or —N(R$^7$)—(CH$_2$)$_m$(CHR$^5$)$_n$—Y—NHC(=NH)NH$_2$;

each of 'm,' 'n,' and 'p' is independently 0, 1, 2, 3, 4, 5, or 6;

$R^5$ is hydroxyl, C1-C6 hydroxyalkyl, carboxyl, C1-C6 carboxyalkyl, amino, or C1-C6 aminoalkyl; and each of $R^6$ and $R^7$ is independently hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, C1-C6 aminoalkyl, or C5-C10 aryl;

allowing the compound to become localized in or around a tissue or organ; and performing a diagnostic, imaging, or visualization procedure on the patient.

2. The method of claim 1, wherein the diagnostic procedure is monitoring hemostasis.

3. The method of claim 1, wherein the diagnostic procedure is imaging vulnerable plaques.

4. The method of claim 1, wherein the diagnostic procedure is tumor imaging.

* * * * *